(12) United States Patent
Helfer et al.

(10) Patent No.: US 6,969,455 B1
(45) Date of Patent: Nov. 29, 2005

(54) ELECTROPHORESIS FRAME FOR GEL SLABS WITH DIFFERENT THICKNESS HOLDER PLATES

(76) Inventors: Joel Helfer, 392 Jinney Hill Rd., Cheshire, CT (US) 06410; James McGuffick, 230 Long Hill Cross Rd., Shelton, CT (US) 06484

( * ) Notice: Subject to any disclaimer, the term of this patent is extended or adjusted under 35 U.S.C. 154(b) by 252 days.

(21) Appl. No.: 10/348,993

(22) Filed: Jan. 22, 2003

(51) Int. Cl.⁷ ......................................... G01N 27/453
(52) U.S. Cl. ................................................... 204/618
(58) Field of Search ............................... 204/466, 467, 204/616–618

(56) References Cited

U.S. PATENT DOCUMENTS

| | | | |
|---|---|---|---|
| 4,518,476 A | 5/1985 | Delony et al. | 204/618 |
| 5,242,568 A | 9/1993 | Ehr et al. | 204/607 |
| 5,415,752 A | 5/1995 | Boquet | 264/104 |
| 5,626,735 A | 5/1997 | Chu | 204/606 |
| 5,632,877 A | 5/1997 | Van Atta | 204/618 |
| 5,656,145 A | 8/1997 | Nguyen et al. | 204/618 |
| 6,162,342 A | 12/2000 | Perez et al. | 204/619 |
| 6,193,868 B1 | 2/2001 | Hsu | 204/168 |
| 2002/0027078 A1 | 3/2002 | Anderson et al. | |

Primary Examiner—Alex Noguerola
(74) Attorney, Agent, or Firm—Fattibene & Fattibene; Paul A. Fattibene; Arthur T. Fattibene

(57) ABSTRACT

A frame used in clamping gel slab holders having different thicknesses used in electrophoresis. The frame has a cam that, when rotated, presses against a plate of a gel slab holder. The cam has a high lobe and a low lobe for selectively clamping gel slab holders having different thicknesses. A thin gel slab holder is securely held in position by rotating the cam in a direction such that the high lobe contacts the thin gel slab holder. A thicker gel slab holder is clamped in position by rotating the cam such that the low lobe contacts the thicker gel slab holder. Gel slab holders having different thicknesses are accommodated.

15 Claims, 6 Drawing Sheets

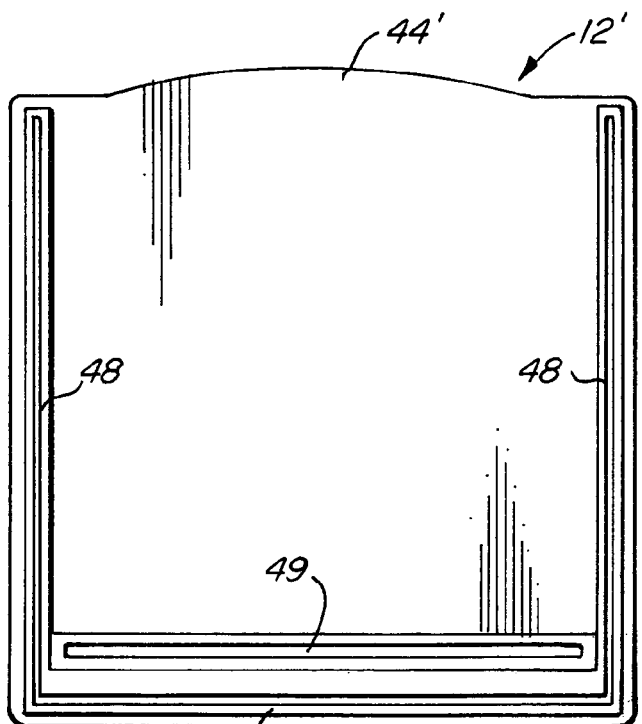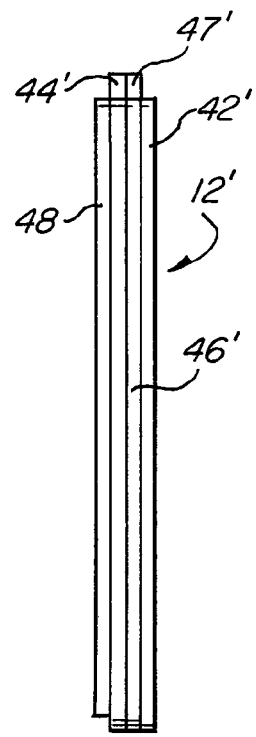
FIG. 4A  FIG. 4B
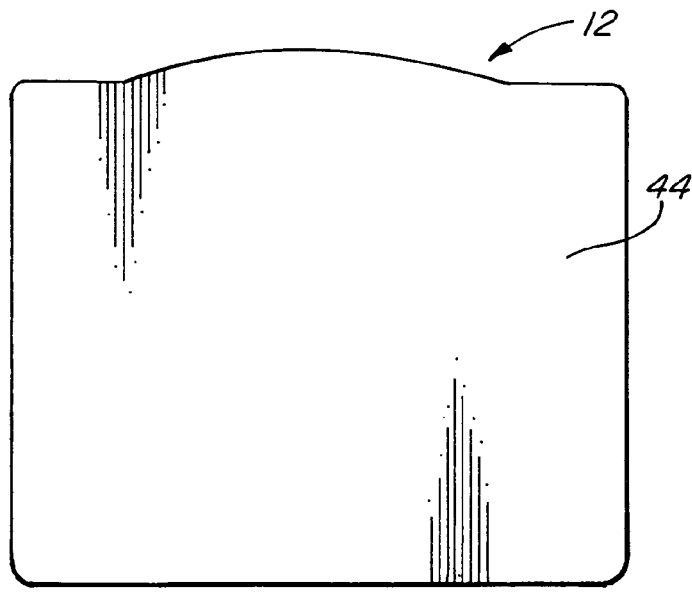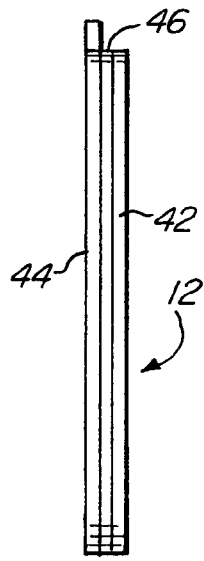
FIG. 5A  FIG. 5B

_US 6,969,455 B1_

ELECTROPHORESIS FRAME FOR GEL SLABS WITH DIFFERENT THICKNESS HOLDER PLATES

FIELD OF THE INVENTION

The present invention relates generally to a frame for holding plates containing gel slabs for use in electrophoresis, and more particularly to a frame for accommodating gel slab plates having different thicknesses.

BACKGROUND OF THE INVENTION

In electrophoresis, electrically charged particles in a solution are caused to move in the presence of an applied electric field. The particles move toward the electrode of opposite electrical polarity. Gel slabs are often used to improve the resolving power of electrophoresis. Gel slabs have been widely adopted and allow for more stable separation and are often used in determining the molecular weights of proteins in biochemical studies.

One such electrophoresis device is disclosed in U.S. Pat. No. 5,632,877 entitled "Rapid Assembly Electrophoresis Cell For Slab Gels" issuing to Van Ata on May 27, 1997. Therein disclosed is an electrophoresis device containing an inner frame holding a gel slab. The inner frame is inserted into an outer clamping frame in which the pressure between the gel enclosure and the inner frame is maintained by a cam operated pressure plate. This entire assembly is then placed in a tank with a buffer solution.

Another electrophoresis device is disclosed in U.S. Pat. No. 6,193,868 entitled "Electrophoretic Separating and Blotting Apparatus" issuing Feb. 27, 2001 to Hsu. Therein disclosed is a frame held within a rack. The rack comprises a plurality of hold down elements adjusted to evenly press on a pressure block against glass plates. The rack is held within a positioning unit and placed in a casing or tank.

The use of pre-cast gel slabs contained in holder plates is widely accepted in electrophoresis. Pre-cast gel slabs are convenient and eliminate the need for a technician to make their own gel slabs. A casting system for making gel slabs is disclosed in U.S. Pat. No. 6,162,342 entitled "Rapid Assembly Casting System For Slab Gels" issuing Dec. 19, 2000 to Perez et al. Therein disclosed is a clamping frame for holding flat plates that serve as a mold for slab gels.

While the use of pre-cast gel slabs is convenient, they are often made in different sizes. For example, 8 cm×10 cm pre-cast gel slabs and 10 cm×10 cm pre-cast gel slabs are popular. However, these gel slabs have different thickness. Therefore, there are problems in mounting these different thickness pre-cast gel slabs in a single electrophoresis apparatus. Often, multiple electrophoresis apparatus are needed to accommodate the different size pre-cast gel slab holders that have different thicknesses. It is time consuming to adjust different electrophoresis apparatus that could accommodate multiple thicknesses of pre-cast gel slab holders. Additionally, it is often difficult to insert the pre-cast gel slab holders within an electrophoresis device without disassembling the electrophoresis device so as to insert the pre-cast gel slab holder. The complication of accommodating a variety of different gel slab holders having different thicknesses is often time costly and time consuming, preventing the efficient use of a laboratory technician's time.

Therefore, there is a need for an electrophoresis device that can quickly put in position and hold pre-cast gel slab holders having different thicknesses.

SUMMARY OF THE INVENTION

The present invention relates to a frame for holding pre-cast gel slab holders in position for use in electrophoresis. The electrophoresis frame comprises a plurality of slots adapted to receive a pre-cast gel slab holder of different thicknesses. A rotating cam is aligned with two edges of the pre-cast gel slab holder. The rotating cam has two lobes having different heights or distances from the axis of rotation. Depending upon the thickness of the pre-cast gel slab holder being used, the cam is rotated in a direction for utilizing the low or short lobe portion of the cam or the high or long lobe portion of the cam. The lobes of the cam force the sides adjacent the edges of the pre-cast gel slab holders against a gasket stop securely sealing and holding in position the pre-cast gel slab holder.

Accordingly, it is an object of the present invention to provide a frame for holding or locking into position pre-cast gel slab holders having different thicknesses.

It is another object of the present invention to accommodate pre-cast gel slab holders from different manufacturers.

It is an advantage of the present invention that it can interchangeably and selectively hold different thickness pre-cast gel slide holders without modification.

It is a further advantage of the present invention that pre-cast gel slab holders having different thicknesses can be held without any modification or disassembly of the frame.

It is a feature of the present invention that a multi lobe cam is used for holding a side along two edges of the pre-cast gel slab holder.

It is another feature of the present invention that a different lobe is selectively rotated into position depending upon the thickness of the pre-cast gel slab holder.

These and other objects, advantages and features will become more readily apparent in view of the following, more detailed description.

BRIEF DESCRIPTION OF THE DRAWINGS

FIG. 4a is a front elevational view of a pre-cast gel slab holder.

FIG. 4b is a side elevational view of a pre-cast gel slab holder illustrated in FIG. 4a and having a thickness D.

FIG. 5a is a front elevational view of another pre-cast gel slab holder.

FIG. 5b is a side elevational view of the pre-cast gel slab holder illustrated in FIG. 5a and having a different thickness d.

DETAILED DESCRIPTION OF THE PREFERRED EMBODIMENTS

Figure 1:
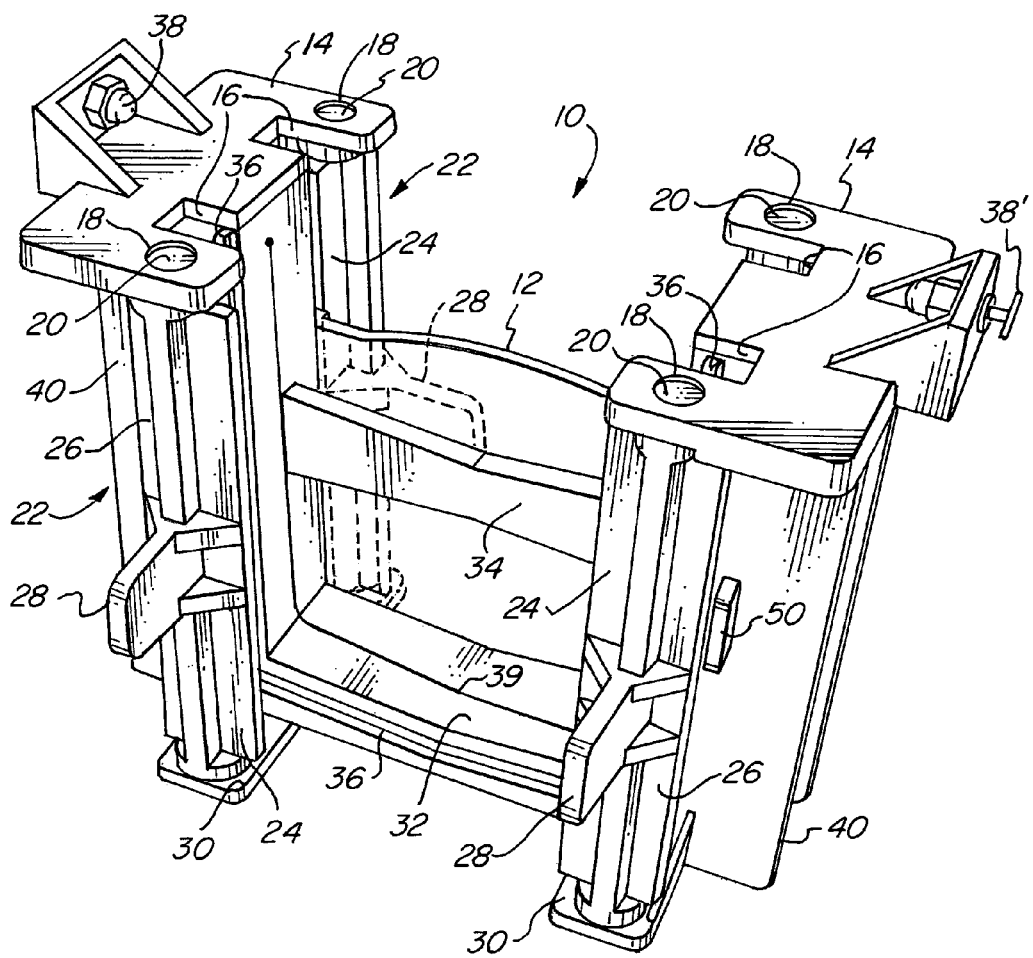
FIG. 1 is a perspective view of an electrophoresis frame of the present invention.

FIG. 1 is a perspective view illustrating the electrophoresis frame 10 of the present invention. Placed within the electrophoresis frame 10 is a pre-cast gel slab holder 12. Slots 16 are formed within top plates 14. The slots 16 have a width sufficient to accommodate the thickness of the gel slab holder 12. Also formed within the top plates 14 are holes 18. The holes 18 rotatably receive pins 20 formed at each end of a cam 22. Bottom plates 30 similarly have holes holding a pin such that cam 22 can be rotated clockwise or counterclockwise. An intermediate support 34 and a bottom support 32 are attached to side supports 40. A frame is thereby formed with two slots for receiving a pre-cast gel slab holder 12.

Placed on each cam 22 are two lobes, a high lobe 24 and a low lobe 26. A handle 28 is used to rotate the cam and the high lobe 24 or the low lobe 26 into position adjacent the slots 16 formed within the top plates 14 and opposite a gasket stop 36. The gasket stop 36 extends along three sides forming an inner compartment once the gel slab holder 12 is in position. Guide tabs 50 aid in positioning and retaining the gel slab holder 12 within the frame 10 before locking the gel slab holder 12 in position against the gasket stop 36. The high lobe 24 has a radial distance from the axis of rotation of cam 22 that is greater than the radial distance from the axis of rotation of low lobe 26. This makes possible the accommodation or holding of a gel slab holder 12 having different thicknesses.

Electrical contacts 38 and 38' provide an electric potential for performing electrophoresis. Electrical contact 38 is coupled to the electrode wire 39. Electrode wire 39 provides a negative potential for the inner chamber formed between two gel slab holders 12 when clamped in position. Electrical contact 38' is coupled to an electrode on the exterior of the electrophoresis frame 10 and provides a positive voltage to the electrode. The frame 10 is placed in a tank or container containing a buffer solution. The frame 10 and cams 22 may be made of any suitable material, such as plastic.

Figure 2:
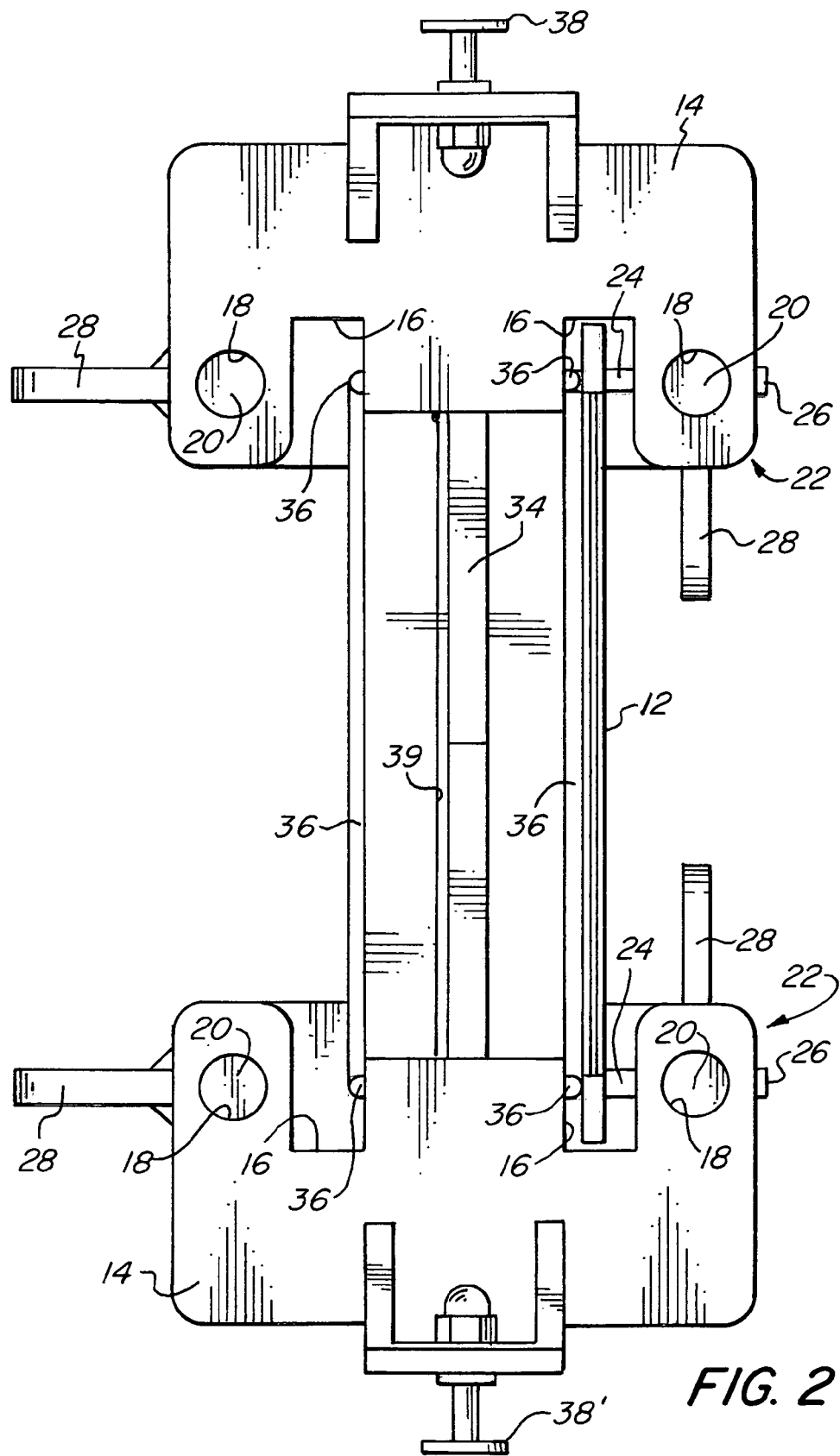
FIG. 2 is a plan view of the electrophoresis frame.

FIG. 2 is a plan view illustrating the positioning of a gel slab holder 12 in position below on slot 16. The gel slab holder 12 is placed between slots 16 and is held or locked into position between gasket stops 36 on one side and the high lobe 24 of cams 22 on the other side along two edges of the gel slab holder 12. When a thicker gel slab holder is utilized, low lobe 26 is used to accommodate the greater distance or thickness.

Figure 3:
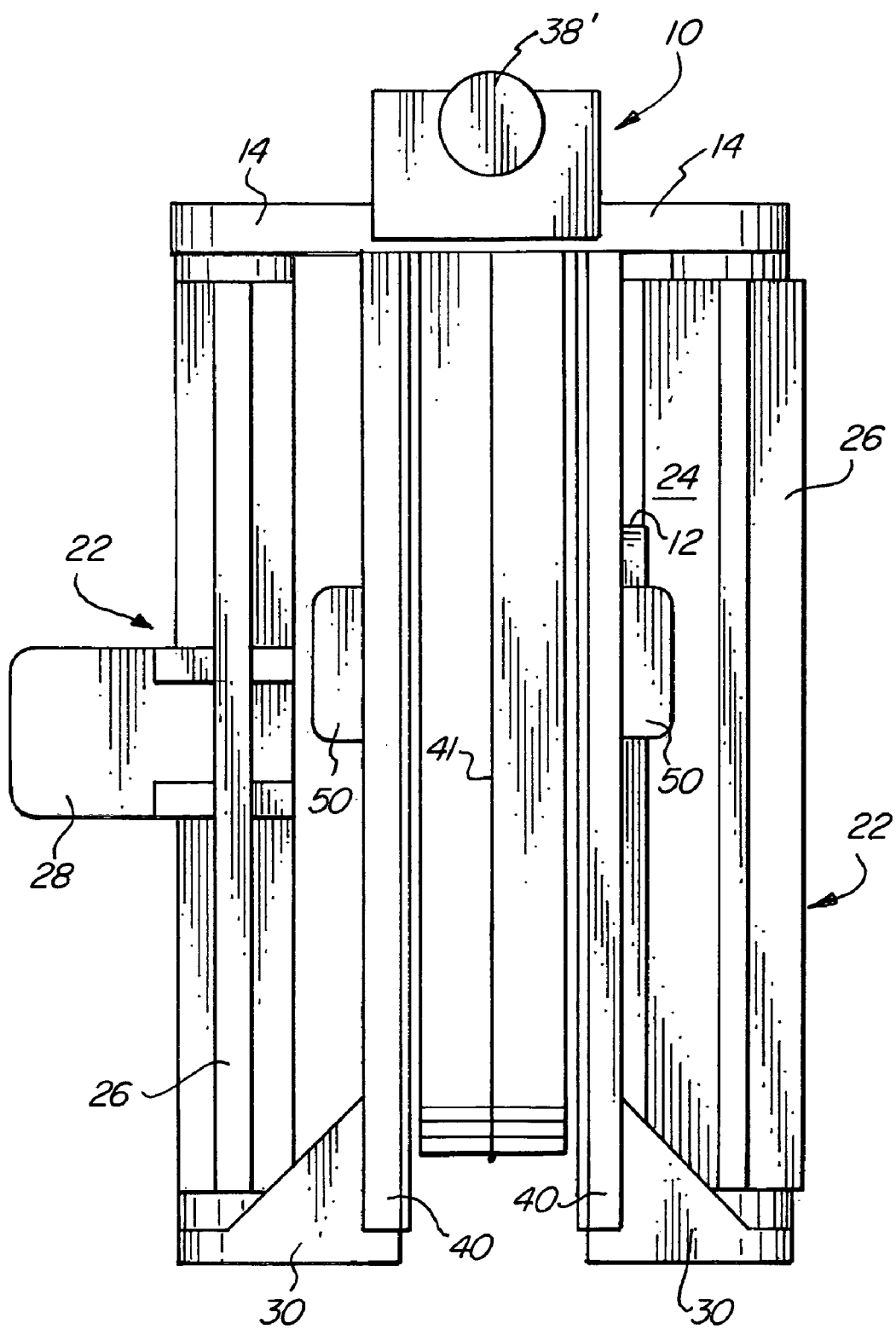
FIG. 3 is an side elevational view of the electrophoresis frame.

FIG. 3 is a side elevational view illustrating the end or side of the electrophoresis frame 10. High lobe 24 contacts the planar surface of gel slab holder 12 along on edge. The low lobe 26 is positioned opposite the high lobe 24. Upon rotating the cam 22, the high lobe 24 or the low lobe 26 can be selectively placed in position, depending upon the thickness of the gel slab holder 12 placed in possition. In this view, electrode wire 41 is shown. Electrode wire 41 is coupled to the positive electrical contact 38'. The tabs 50 prevent lateral movement of the gel slab holder 12 and helps in positioning the gel slab holder 12 prior to clamping holding with the lobes 24 and 26 of cams 22.

FIGS. 4a–b illustrate one type of pre-cast gel slab holder 12'. The pre-cast gel slab holder 12' has spacers 48 around three peripheral edges. Additionally, a lower slit 49 is formed within plate 44'. In FIG. 4b, the structure showing the thickness D of the gel slab holder 12' is more clearly illustrated. Plates 42' and 44' have a gap in which a gel slab 46' is formed. A comb 47' may be inserted at the top of the gel slab 46'. The thickness of edges of the gel slab holder 12' is represented by dimension D.

FIGS. 5a–b illustrate another type of gel slab holder 12. The gel slab holder 12 has a plate 42 and a plate 44 with a gel slab 46 cast there between. The gel slab holder 12 has a thickness d. Thickness d is less than thickness D illustrated in FIG. 4b. The plates 42 and 44 are generally transparent.

FIGS. 4a–b and 5a–b illustrate different types of gel slab holders that may be utilized or held within the present invention.

Figure 6:
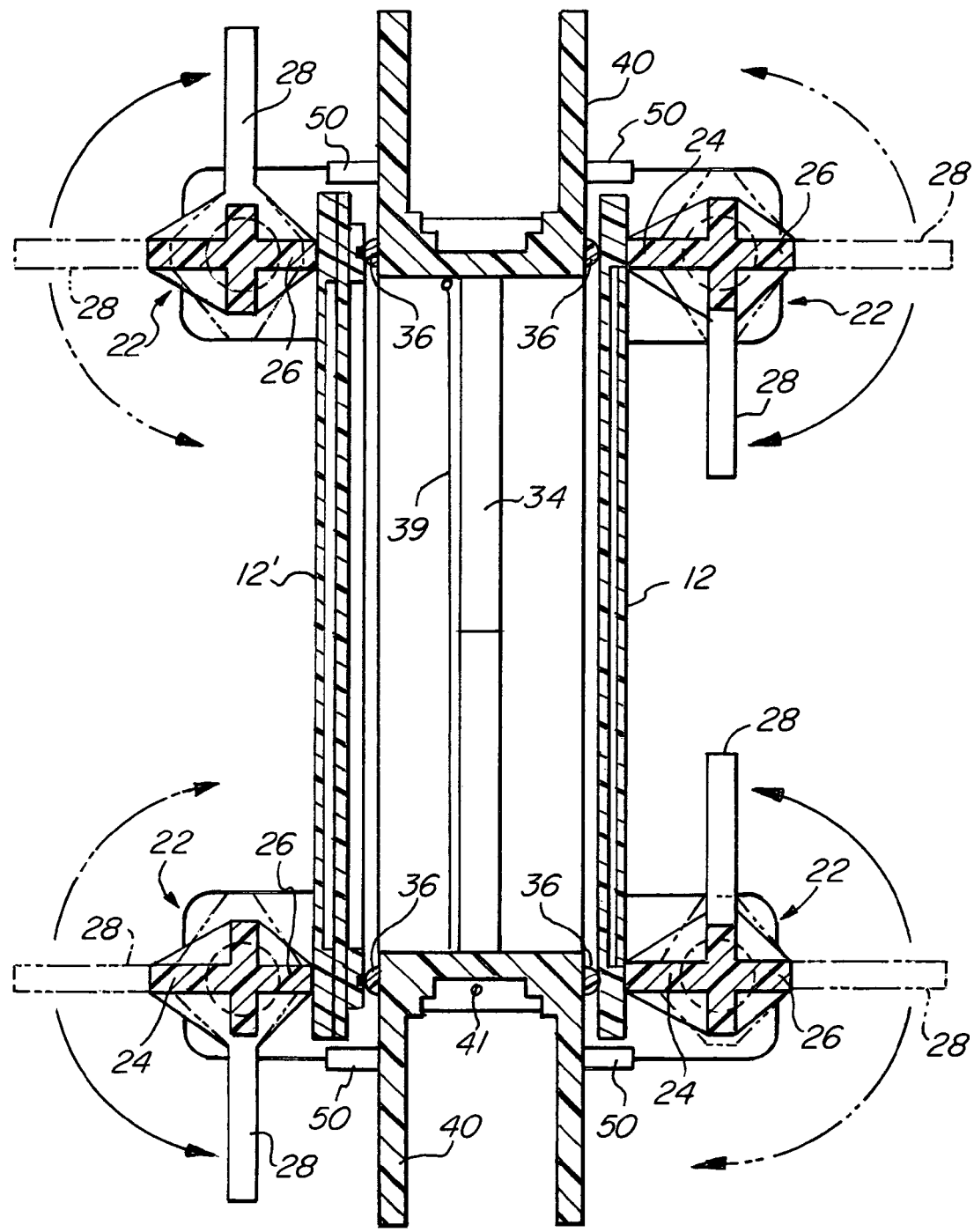
FIG. 6 is a cross-section of the electrophoresis frame illustrating the holding of pre-cast gel slab holders having different thicknesses.

FIG. 6 is a partial cross-section illustrating the present invention holding gel slab holders having different thicknesses. On one side, cams 22 are rotated such that the high lobe 24 contacts the gel slab holder 12, pressing it against the gasket stops 36. The handles 28 of the cams 22 are rotated inward towards each other. On the other side, gel slab holder 12', having a thickness greater than that of gel slab holder 12, is held by cams 22 rotated such that the low lobe 26 contacts the edges of the gel slab holder 12'. The handles 28 of the cams 22 are rotated outward away from each other to hold gel slab holder 12'. The gel slab holder 12' is pressed against gaskets 36 by low lobes 26 of cams 22. The handles 28 are rotate outward moving the low lobe 26 into position against the gel slab holder 12'. Between the gel slab holder 12 and gel slab holder 12' an inner chamber is formed. The high lobes 24 and low lobes 26 extend along a substantial portion of the gasket stop 36. This helps to seal the inner chamber. The high lobes 24 and low lobes 26 preferably extend along the entire length of two of the three sides of said gasket stop 36.

Figure 7:
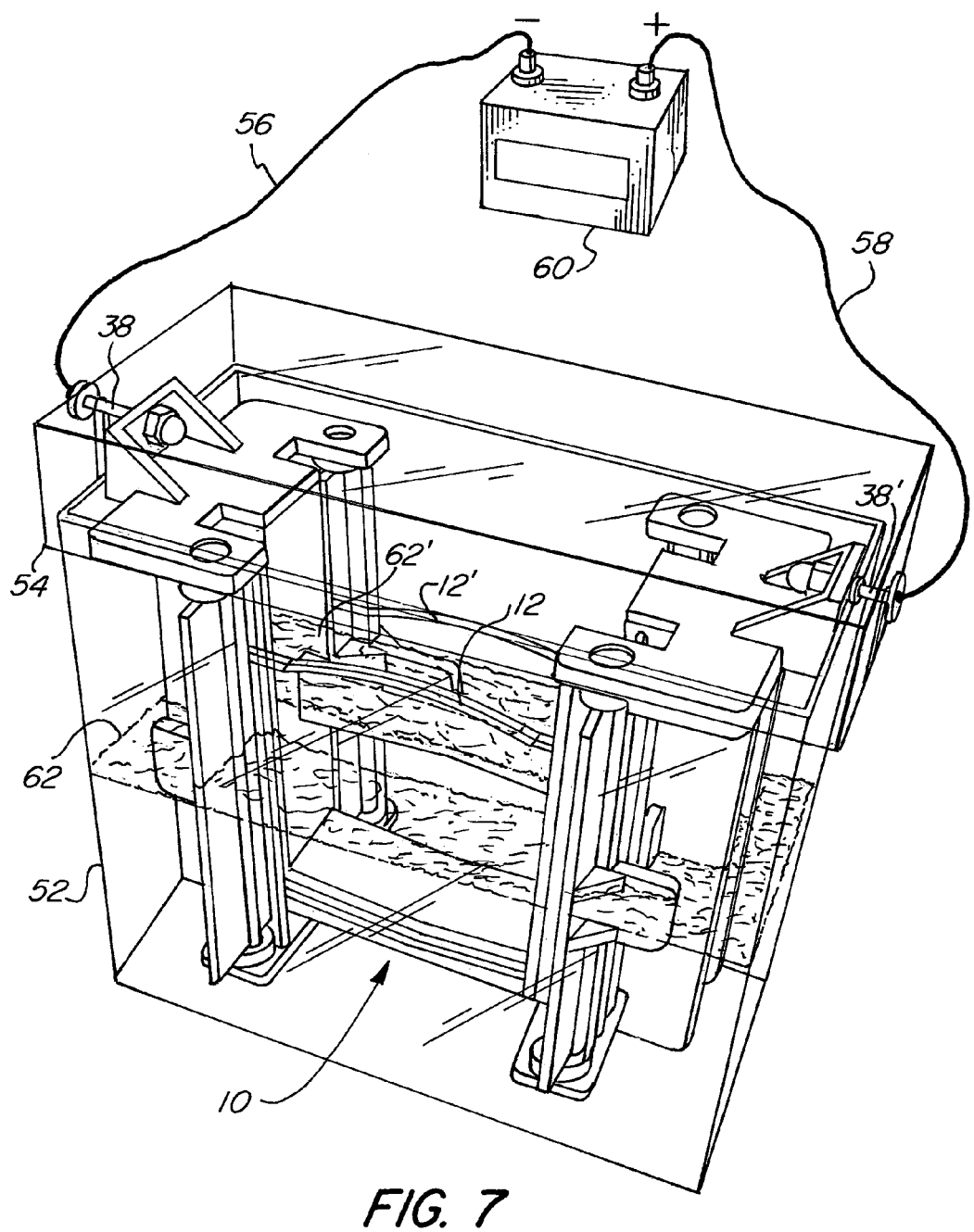
FIG. 7 schematically illustrates the positioning of the electrophoresis frame of the present invention in an electrophoresis apparatus.

FIG. 7 illustrates the operation of the electrophoresis frame 10 in an electrophoresis device. A tank 52 contains the electrophoresis frame 10. The electrophoresis frame 10 holds a gel slab holder 12 and a gel slab holder 12', forming an inner chamber. It should be appreciated that the electrophoresis frame 10 is capable of holding two of the same or different gel slab holders depending upon the procedure being performed. Contained within the inner chamber is a buffer solution 62'. An outer chamber is formed between the tank 52 and the electrophoresis frame 10 holding additional buffer solution 62. Placed on top of the tank 52 is a cover 54. Cover 54 has contacts contacting electrical contacts 38 and 38'. Electrical contact 38' is coupled by wire 58 to a positive terminal of a voltage supply or battery 60. Electrical contact 38 is coupled by wire 56 to a negative terminal of the voltage supply or battery 60. Accordingly, electrical contact 38' provides a positive potential to buffer solution 62 and electrical contact 38 provides a negative potential to buffer solution 62'. As a result of the difference in potential, electrophoresis occurs when the buffer solution 62 is brought in contact with the bottom of the gel slab contained within the gel slab holders 12 and 12' and the buffer solution 62' is brought into contact with the top of the gel slab contained within the gel slab holders 12 and 12'. Additionally, the electrophoresis may be accomplished by other known equivalent methods.

The present invention, in utilizing a multi lobe cam, can easily accommodate gel slab holders having different thicknesses. Accordingly, a single electrophoresis frame may be utilized to accommodate different gel slab holders from different manufacturers or for different procedures without any disassembly or modification. The present invention can also switch between different thickness gel slab holders simply by selecting the direction of rotation of the cams to clamp the gel slab holders securely into position. Therefore, the present invention greatly reduces the different apparatuses necessary for performing electrophoresis and makes quick and easy the interchange of different gel slab holders with different thicknesses.

While the present invention has been described with respect to a particular embodiment, it should be appreciated by those skilled in the art that various modifications may be made without departing from the spirit and scope of this invention.

What is claimed is:

1. An electrophoresis frame accommodating gel slab holders of different thicknesses comprising:
   a top plate;
   a bottom plate;
   a side support;
   a rotating cam held between said top plate and said bottom plate;
   a high lobe formed on said cam; and
   a low lobe formed on said cam,
   whereby one of the gel slab holders is capable of being secured between either said high lobe or said low lobe and said side support.

2. An electrophoresis frame as in claim 1 further comprising:
   a slot placed in said top plate adapted to receive one of the gel slab holders.

3. An electrophoresis frame as in claim 1 further comprising:
   a gasket stop placed opposite said rotating cam.

4. An electrophoresis frame as in claim 1 further comprising:
   a pair of electrical contacts attached to said top plate.

5. An electrophoresis frame as in claim 4 further comprising:
   an electrode wire attached to each of said pair of electrical contacts.

6. An electrophoresis frame accommodating gel slab holders of different thicknesses comprising:
   a top plate having slots therein adapted to receive one of the gel slab holders;
   a bottom plate;
   a side support placed between said top plate and said bottom plate;
   a gasket stop placed along an edge of said side support;
   a rotating cam held between said top plate and said bottom plate opposite said gasket stop;
   a high lobe formed on said cam; and
   a low lobe formed on said cam;
   whereby one of the gel slab holders is capable of being secured between either said high lobe or said low lobe and said side support depending upon the thickness of the one of the gel slab holders.

7. An electrophoresis frame as in claim 6 further comprising:
   a handle on said cam.

8. An electrophoresis frame as in claim 6 further comprising:
   a guide tab placed on said side support, whereby the one of the gel slab holders is prevented from moving laterally.

9. An electrophoresis frame as in claim 6 wherein:
   said high and low lobe extend along a substantial length of said gasket stop.

10. A frame for holding gel slab holders used in electrophoresis comprising:
    a support having two sides;
    a first pair of rotating cams pivotally attached to said support adjacent one of the two sides, each of said first pair of rotating cams having a high lobe and a low lobe capable of being rotated into position adjacent said support, whereby different gel slab holders having different thicknesses are capable of being held between either the high lobe or the low lobe and said support; and
    a second pair of rotating cams attached to said support adjacent one of the two sides, each of said second pair of rotating cams having a high lobe and a low lobe capable of being rotated into position adjacent said support, whereby different gel slab holders of different thicknesses are capable of being held between either the high lobe or the low lobe and said support.

11. A frame for holding gel slab holders used in electrophoresis as in claim 10 further comprising:
    a stop gasket placed adjacent said first pair and second pair of rotating cams.

12. A frame for holding gel slab holders used in electrophoresis as in claim 10 further comprising:
    a handle formed on said first pair and second pair of rotating cams.

13. A frame for holding gel slab holders used in electrophoresis as in claim 10 further comprising:
    electrical contacts placed on said support.

14. A frame for holding gel slab holders used in electrophoresis as in claim 10 wherein:
    the high and low lobes of said first pair and second pair of cams extend along a substantial length of said first pair and second pair of cams.

15. An electrophoresis device comprising:
    a tank;
    a frame placed within said tank, said frame having two sides;
    electrical contacts placed on said frame;
    a pair of rotating cams placed on the two sides of said frame;
    a pair of lobes having different radial lengths formed on each of said pair of rotating cams, whereby upon rotating each of said pair of rotating cams each of said pair of lobes is capable of being positioned adjacent one of the two sides of said frame;
    a first gel slab holder place between one of the two sides and a first selected one of said pair of rotating cams, the first selected one of said pair of rotating cams being selected based upon a thickness of said first gel slab holder;
    a second gel slab holder placed between one of the two sides and a second selected one of said pair of rotating cams, the second selected one of said pair of rotating cams being selected based upon a thickness of said second gel slab holder; and
    a cover adapted to be placed on said frame,
    whereby different gel slab holders having different thickness are capable of being held within said frame by said pair of rotating cams.

* * * * *